(12) United States Patent
Kim et al.

(10) Patent No.: US 10,478,470 B2
(45) Date of Patent: Nov. 19, 2019

(54) PHARMACEUTICAL COMPOSITION CONTAINING LEUPROLIDE AND HAVING BOTH IMMEDIATE AND SUSTAINED RELEASE PROPERTIES

(71) Applicant: SK Chemicals Co., Ltd., Gyeonggi-do (KR)

(72) Inventors: Hong Kee Kim, Gyeonggi-do (KR); Kyu Ho Lee, Seoul (KR); Seok Hyun Hong, Gyeonggi-do (KR); Yong-kyu Kwak, Seoul (KR); Ho Chul Shin, Gyeonggi-do (KR); Hun-Teak Kim, Seoul (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 3 days.

(21) Appl. No.: 15/417,348

(22) Filed: Jan. 27, 2017

(65) Prior Publication Data

US 2017/0196932 A1  Jul. 13, 2017

Related U.S. Application Data

(63) Continuation of application No. PCT/KR2015/007874, filed on Jul. 28, 2015.

(30) Foreign Application Priority Data

Jul. 28, 2014 (KR) .................. 10 2014 0095977

(51) Int. Cl.

| A61K 38/09 | (2006.01) |
|---|---|
| A61K 9/16 | (2006.01) |
| A61K 31/409 | (2006.01) |
| A61K 31/445 | (2006.01) |
| A61K 9/00 | (2006.01) |
| A61K 9/50 | (2006.01) |

(52) U.S. Cl.
CPC ............ *A61K 38/09* (2013.01); *A61K 9/0019* (2013.01); *A61K 9/16* (2013.01); *A61K 9/5031* (2013.01); *A61K 31/409* (2013.01); *A61K 31/445* (2013.01)

(58) Field of Classification Search
CPC .... A61K 38/00; A61K 9/0019; A61K 9/5089; A61K 2800/48; A61K 31/00; A61K 49/0056
See application file for complete search history.

(56) References Cited

U.S. PATENT DOCUMENTS

| 6,534,094 B2 * | 3/2003 | Moyano ............... A61K 9/5031 264/4.1 |
|---|---|---|
| 2002/0054907 A1 | 5/2002 | Devane et al. |

FOREIGN PATENT DOCUMENTS

| CN | 106794147 A | 5/2017 |
|---|---|---|
| EP | 3175847 A1 | 6/2017 |
| JP | 2014513720 A | 6/2014 |
| JP | 2017522336 A | 8/2017 |
| KR | 20000032631 A | 6/2000 |
| KR | 10-2004-0066191 A | 7/2004 |
| KR | 100545287 B1 | 1/2006 |
| KR | 20060125749 A | 12/2006 |
| KR | 100802625 B1 | 2/2008 |
| KR | 2010044238 A | 4/2010 |
| KR | 101085729 B1 | 11/2011 |
| KR | 101108439 B1 | 1/2012 |
| KR | 101359092 B1 | 2/2014 |
| KR | 101367929 B1 | 2/2014 |
| KR | 101438549 B1 | 11/2014 |
| KR | 101487953 B1 | 2/2015 |
| KR | 101686986 B1 | 12/2016 |
| WO | WO 2004/098513 A2 | 11/2004 |
| WO | WO 2009/037539 A2 | 3/2009 |

OTHER PUBLICATIONS

Reinhold et al. Self-healing microencapsulation of biomacromolecules without organic solvents. Angew Chem Int Ed Engl. Oct. 22, 2012;51(43):10800-3. (Year: 2012).*
Luan et al. Key parameters affecting the initial release (burst) and encapsulation efficiency of peptide-containing poly(lactide-co-glycolide) microparticles. Int J Pharm. Nov. 6, 2006;324(2):168-75. (Year: 2006).*
Mark A. Mitchell. Therapeutic Review Leuprolide acetate. Seminars in Avian and Exotic Pet Medicine, vol. 14, No. 2 Apr. 2005: pp. 153-155. (Year: 2005).*
Lupron Depot. 2012. (Year: 2012).*
International Search Report and Written Opinion of the International Searching Authority corresponding to Korean Paten Application No. PCT/KR2015/007874 dated Nov. 2, 2015.
Notification Concerning Transmittal of International Preliminary Report on Patentability corresponding to Korean Paten Application No. PCT/KR2015/007874 dated Feb. 9, 2017.

(Continued)

*Primary Examiner* — Marcela M Cordero Garcia
*Assistant Examiner* — Jia-Hai Lee
(74) *Attorney, Agent, or Firm* — Jenkins, Wilson, Taylor & Hunt, P.A.

(57) ABSTRACT

The present invention relates to a pharmaceutical composition containing leuprolide acetate and having both immediate and sustained release properties and, more specifically, to a pharmaceutical composition in which, on the basis of the total weight of active ingredients, leuprolide as an immediate release preparation is contained in 0.001 wt % to 25 wt %; and leuprolide contained in microspheres of a sustained release preparation is contained in 75 wt % to 99.999 wt %. The pharmaceutical composition of the present invention is characterized by satisfying both a drug immediate release property so as to realize the prompt exposure to a sufficient amount of drug at the early stage for expression of medicinal effects and a drug sustained release property for four weeks or longer, and the pharmaceutical composition is effective in the prevention and treatment of sex hormone-dependent positive or malignant diseases.

6 Claims, 2 Drawing Sheets

(56) References Cited

OTHER PUBLICATIONS

Ogawa et al., "Controlled Release of LHRH Agonist, Leuprolide Acetate, from Microcapsules: Serum Drug Level Profiles and Pharmacological Effects in Animals," Journal of Pharmacy and Pharmacology, vol. 41, No. 7, pp.439-444 (Jul. 1989).

Okada et al., "Vaginal absorption if a potent luteinizing hormone-releasing hormone analogue (leuprolide) in rats IV: Evaluation of the vaginal absorption and gonadotropin responses by radioimmunoassay," J Pharmaceutical Sciences, vol. 73, No. 3, pp. 298-302 (Mar. 1984).

Extended European Search Report corresponding to European Patent Application No. 15827054.6 date Feb. 20, 2018.

International Preliminary Report on Patentability corresponding to Korean Patent Application No. PCT/KR2015/007874 dated Jan. 31, 2017.

Office Action corresponding to Korean Patent Application Serial No. 10-2014-0095977 dated Nov. 27, 2014; retrieved from Global Dossier on Nov. 7, 2018.

Office Action corresponding to Korean Patent Application Serial No. 10-2014-0095977 dated May 15, 2015; retrieved from Global Dossier on Nov. 7, 2018.

Office Action corresponding to Korean Patent Application Serial No. 10-2014-0095977 dated Jan. 4, 2016; retrieved from Global Dossier on Nov. 7, 2018.

Office Action corresponding to Korean Patent Application Serial No. 10-2014-0095977 dated Feb. 18, 2016; retrieved from Global Dossier on Nov. 7, 2018.

Office Action corresponding to Korean Patent Application Serial No. 10-2014-0095977 dated Oct. 19, 2016; retrieved from Global Dossier on Nov. 7, 2018.

* cited by examiner

[FIG. 1]
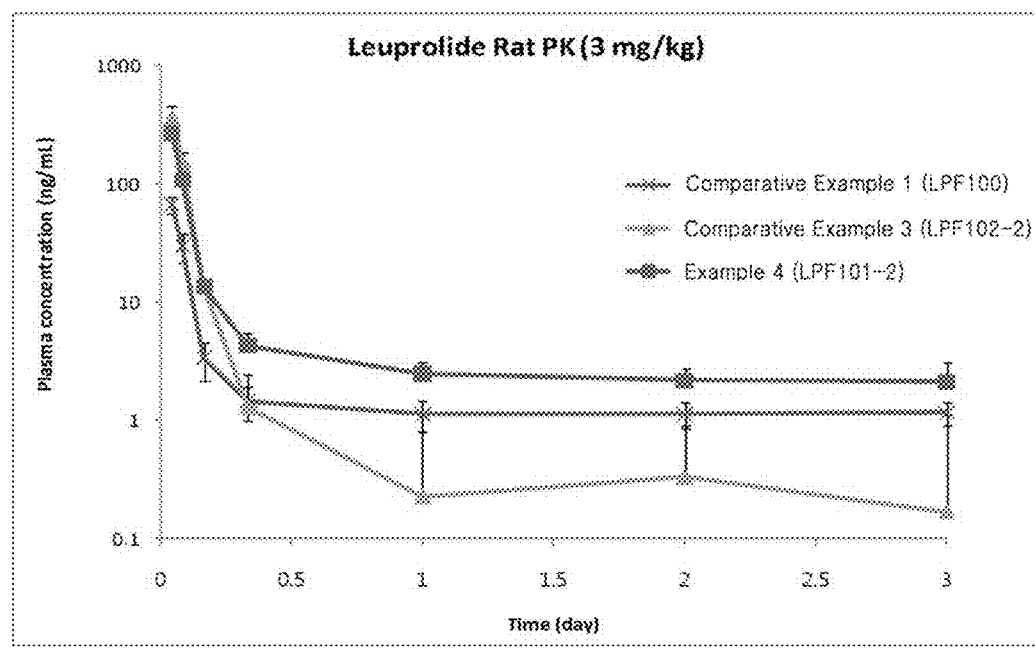

[FIG. 2]
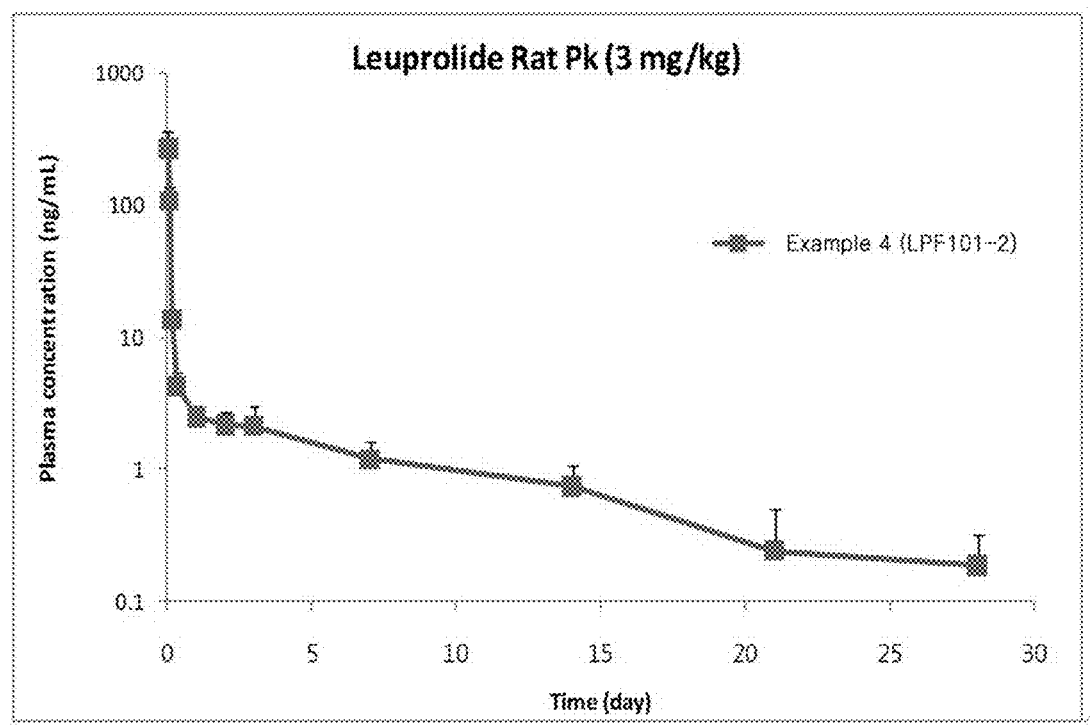

PHARMACEUTICAL COMPOSITION CONTAINING LEUPROLIDE AND HAVING BOTH IMMEDIATE AND SUSTAINED RELEASE PROPERTIES

CROSS REFERENCE TO RELATED APPLICATIONS

The presently disclosed subject matter is a continuation of and claims the benefit of PCT International Patent Application Serial No. PCT/KR2015/007874, filed Jul. 28, 2015, which claims the benefit of Korean Patent Application Serial No. 10-2014-0095977, filed Jul. 28, 2014, the disclosures of which are incorporated herein by reference in their entireties.

TECHNICAL FIELD

This application claims a priority from Korean Patent Application No. 10-2014-0095977 filed on Jul. 28, 2014, the entire contents of which are incorporated herein by reference.

The present invention relates to a pharmaceutical composition comprising leuprolide with both immediate and sustained release properties. More particularly, the present invention relates to a pharmaceutical composition comprising leuprolide as an immediate release preparation in an amount of 0.001 wt % to 25 wt %, and leuprolide as contained in a microsphere of a sustained-release preparation in an amount of 75 wt % to 99.999 wt %, on the basis of a total weight of active ingredients.

BACKGROUND ART

LHRH (luteinizing hormone-releasing hormone), also known as GnRH (gonadotropin releasing hormone), is a hypothalamic decapeptide (pGlu-His-Trp-Ser-Tyr-Gly-Leu-Arg-Pro-Gly-NH$_2$) that regulates the reproductive system of vertebrates. It is released into the capillaries of the hypothalamus-pituitary portal system of the median eminence and the infundibular stalk. By this capillary network, LHRH reaches the anterior pituitary gland and then the gonadal stimulated target cells by the second capillary network. GnRH acts at the membrane level of target cells through receptors with seven transmembrane segments that are coupled to phospholipase C via G proteins to increase intracellular calcium flux. Its action induces the biosynthesis and release of the gonadotropin FSH (follicle-stimulating hormone) and LH (luteinizing hormone). It has been found that LHRH agonists and antagonists are useful for treating female endometriosis, fibroids, polycystic ovarian syndrome, breast cancer, ovarian cancer, endometrial cancer, gonadotropin-induced pituitary desensitization during a medically assisted delivery protocol, male benign prostate enlargement & polymorphism and prostate cancer, and male or female precocious puberty.

Currently used LHRH (Luteinizing hormone-releasing hormone) agonists are peptide compounds that are required to be administered via intravenous or subcutaneous routes due to their low oral bioavailability. In addition, LHRH agonists should be taken for a long period of time as drugs for chronic diseases. It is necessary that drugs of the LHRH group are required to be exposed in their sufficient amount at an initial stage of administration in order to exhibit their therapeutic effects.

One of the LHRH agonists, leuprolide acetate, has a short half-life upon its conventional subcutaneous or intramuscular injection, resulting in a rapid decrease of its blood concentration after administration and its disappearance within a few hours (See J Pharmaceutical Sciences Vol. 73 No. 3, 1984, pp. 298-302). This led to the inconvenience of its daily administration in order to maintain its efficacy, while its inconvenience has been further exacerbated by its administrative mode of injection.

In order to mitigate this drawback, formulations (i.e. sustained release formulations) with their efficacy duration of 4 weeks or longer have been developed and sold. For the purpose of exhibiting its drug efficacy, leuprolide acetate is required to be exposed in a sufficient amount to target sites at the initial stage of its administration. However, the conventional long-lasting (or sustained release) formulations have not met such a requirement due to the low initial release rate of leuprolide acetate. In particular, considering that leuprolide acetate inhibits the levels of circulating sex hormones for 2 to 4 weeks after its initial rise, it is desirable that the initial release rate of leuprolide acetate from its delivery microparticle is high in order for leuprolide to be effective. According to the Food and Drug Administration, it is indicated that high initial release of leuprolide is required to achieve its fast casting effects.

Therefore, in order for leuprolide to exhibit a sufficient pharmacological effect as an LHRH agonist, there is a need for a leuprolide formulation which satisfies both the rapidity of its efficacy at the initial stage of administration and the sustainability of maintaining its certain blood level for an extended period of time after administration.

PRIOR ART LITERATURES

Non-Patent Document 1: Hiroaki Okada et al., Vaginal absorption of a potent luteinizing hormone-releasing hormone analogue (leuprolide) in rats IV: Evaluation of the vaginal absorption and gonadotropin responses by radioimmunoassay, J Pharmaceutical Sciences Vol. 73 No. 3, 1984, pp. 298-302.

Non-Patent Document 2: Yasuaki Ogawa et al., Controlled Release of LHRH Agonist, Leuprolide Acetate, from Microcapsules: Serum Drug Level Profiles and Pharmacological Effects in Animals, Journal of Pharmacy and Pharmacology, 1989 July; 41 (7): 439-44.

DETAILED DESCRIPTION OF THE INVENTION

Technical Problem

Accordingly, while researching on an LHRH agonist preparation which is able to expose a sufficient amount of its active drug to a target site within a short period of time and maintain its effect at a high level for an extended period of time, the present inventors have confirmed that an injectable preparation comprising a certain proportion of an active drug in a form of microsphere achieves an increased Cmax, a shortened Tmax and an increased initial AUC, while maintaining the blood concentration of the active drug for 4 weeks or longer in one injection, thus completing the present invention.

Thus, an object of the present invention is to provide a pharmaceutical composition comprising leuprolide as an immediate release preparation in an amount of 0.001 wt % to 25 wt %, and leuprolide as contained in a microsphere of a sustained-release preparation in an amount of 75 wt % to 99.999 wt %, on the basis of a total weight of active ingredients.

Technical Solution

In order to achieve the above object of the present invention, an aspect of the present invention provides a pharmaceutical composition comprising leuprolide as an immediate release preparation in an amount of 0.001 wt % to 25 wt %, and leuprolide as contained in a microsphere of a sustained-release preparation in an amount of 75 wt % to 99.999 wt %, on the basis of a total weight of active ingredients.

Hereinafter, the present invention will be described in detail.

An aspect of the present invention provides a pharmaceutical composition comprising leuprolide as an immediate release preparation in an amount of 0.001 wt % to 25 wt %, and leuprolide as contained in a microsphere of a sustained-release preparation in an amount of 75 wt % to 99.999 wt %, on the basis of a total weight of active ingredients.

The pharmaceutical composition according to the present invention comprises leuprolide as an active ingredient, wherein the composition simultaneously comprises leuprolide itself as an immediate release preparation and leuprolide-containing microspheres as a sustained release preparation. The pharmaceutical composition according to the present invention is characterized in that leuprolide is contained at a specific ratio as the immediate release preparation and the sustained release preparation, respectively, on the basis of a total weight of the active ingredient.

As used herein, the term "leuprolide" refers to 5-Oxo-L-prolyl-L-histidyl-L-tryptophanyl-L-seryl-L-tyrosyl-D-leucyl-L-leucyl-L-arginyl-L-prolyl ethylamide as represented by Formula 1 and its pharmaceutically acceptable salts. The leuprolide is also referred to as "Leuprorelin," while those terms are used herein interchangeably.

Leuprolide as used herein may be utilized as per se or in the form of a salt, preferably a pharmaceutically acceptable salt. The term "a pharmaceutically acceptable" as used herein means physiologically acceptable and does not generally cause an allergic reaction or a similar reaction when administered to humans. Preferably, the salt may be and acid-added salt prepared by a pharmaceutically acceptable free acid. As a free acid, an organic acid or inorganic acid may be used. As used herein, the organic acid includes, but is not limited to, citric acid, acetic acid, lactic acid, tartaric acid, maleic acid, fumaric acid, formic acid, propionic acid, oxalic acid, trifluroacetic acid, benzoic acid, gluconic acid, methanesulfonic acid, glycolic acid, succinic acid, 4-toluenesulfonic acid, glutamic acid and aspartic acid. As used herein, the inorganic acid includes, but is not limited to, hydrochloric acid, bromic acid, sulfuric acid, and phosphoric acid.

Preferably, leuprolide according to the present invention may be leuprolide acetate.

In an aspect of the present invention, leuprolide per se as an immediate release preparation may be contained in an amount of 0.001 wt % to 25 wt %, preferably 0.1 wt % to 20 wt %, on the basis of a total weight of active ingredients in the composition.

In the present invention, leuprolide itself as the immediate release preparation may be contained in an amount of 0.001 to 25% by weight, preferably 0.1 to 20% by weight, on the basis of a total weight of active ingredients in the composition.

As used herein, the term "microsphere" means a microsphere containing leuporide which can be commercially obtained or used, or can be produced by known methods in the art of preparing conventional sustained release injectable preparations. Methods for producing the sustained-release injectable preparations may include, but are not limited to, coacervation, melt extrusion, spray drying, solvent extraction, solvent evaporation (including double emulsion evaporation (W/O/W, water/oil/water) and single emulsion evaporation (O/W, oil/water), and the like.

Specifically, the above-mentioned leuprolide-containing microsphere may be prepared by a conventional method for producing a sustained release injectable preparation, the method comprising:

(i) mixing an inner aqueous phase (W1) containing leuprolide, a thickener and an aqueous solvent with an oil phase (O) containing a polymer and a fat-soluble solvent to obtain a W1/O emulsion;

[Formula 1]

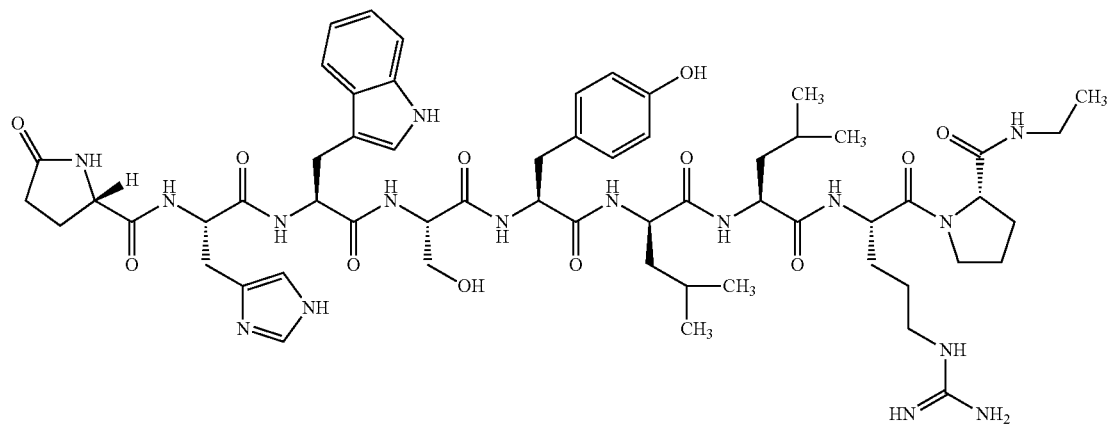

(ii) dispersing the W1/O emulsion of step (i) in a polyvinyl alcohol aqueous solution (W2) to obtain a W1/O/W2 emulsion; and (iii) drying and recovering the W1/O/W2 emulsion prepared in the step (ii).

In the above step (i), the inner aqueous phase (W1) containing leuprolide, the thickener and the aqueous solvent is mixed with the oil phase (O) containing the polymer and the fat-soluble solvent to obtain the W1/O emulsion.

As used herein, the thickener increases the viscosity of the inner aqueous phase so as to produce a W1/O emulsion which possesses an increased viscosity upon cooling.

Examples of the thickener according to the present invention may include a high molecular weight compound (such as casein, gelatin, collagen, albumin and pectin), a carbohydrate (such as cellulose, dextrin and agar), and a natural rubber such as Xanthan gum, while being preferably gelatin.

As used herein, the aqueous solvent refers to a solvent capable of dissolving a water-soluble drug according to the present invention. Any aqueous solvent generally used for drug dissolution may be used without limitation. The aqueous solvent according to the present invention may include, but is not limited to, water, phosphate buffer, acetate buffer, citrate buffer, tris buffer, HEPES buffer, lower alcohols having 1 to 4 carbon atoms (e.g., methanol, ethanol, propanol, etc.), and the like. The aqueous solvent may be preferably ethanol, methanol, water, buffer or a mixture thereof, while being more preferably water.

The weight ratios of the aqueous solvent, leuprolide, and gelatin constituting the inner aqueous phase (W1) may vary depending on the types of the aqueous solvent and the drug. For example, the weight ratios of an aqueous solvent: leuprolide:gelatin for mixing may be 1:(0.01 to 2):(0.01 to 0.5), preferably 1:(0.05 to 1):(0.05 to 0.2), while being not limited thereto.

The inner aqueous phase (W1) may be prepared by mixing an aqueous solvent, leuprolide and gelatin sequentially or simultaneously, while being preferably mixed under heating conditions. The heating temperature may preferably be 30° C. to 80° C., more preferably 50° C. to 70° C.

The polymer is a polymer compound constituting the outer wall of the polymer microsphere. With respect to the polymer according to the present invention, any known polymer compound in the art used for the preparation of polymer microspheres may be used without limitation. Preferably, the polymer may include, but is not limited to, polyesters based on hydroxy fatty acids such as a copolymer of poly(lactic acid) and poly(glycolic acid), a polymer consisting solely of polylactic acid or polylactide, a polylactic-co-glycolic acid, polylactide-co-glycolide (PLGA), polyphosphazene, polyiminocarbonate, polyphosphoester, polyanhydride, polyorthoester, a copolymer of lactic acid and caprolactone, polycaprolactone, polyhydroxyvalerate, polyhydroxybutyrate, polyamino acid, a copolymer of lactic acid and amino acid, and mixtures thereof, while being more preferably a copolymer of poly(lactic acid) and poly(glycolic acid). The weight-average molecular weight of the polymer used in the preparation method of the present invention is not particularly limited, but may be generally in the range of 2,000 to 100,000, preferably 5,000 to 50,000, and more preferably 8,000 to 30,000.

The molar ratio of the lactic acid and the glycolic acid in the copolymer (PLGA) of the poly(lactic acid) and the poly(glycolic acid) may be (0 to 100):(0 to 100), preferably (50 to 90):(10 to 50) (for example, 50:50, 65:35, 75:25, 85:15, 90:10), and more preferably (70 to 80):(20 to 30) (for example, 75:25).

As used herein, the fat-soluble solvent is used to dissolve high-molecular-weight polymers. Generally, any fat-soluble solvent used for preparing polymer microspheres for sustained-release preparations may be used without limitation. Examples of the fat-soluble solvent according to the present invention include halogenated hydrocarbons such as dichloromethane, chloroform, dichloroethane, trichloroethane and carbon tetrachloride; ethers such as ethyl ether and isopropyl ether; fatty esters such as ethyl acetate and butyl acetate; and aromatic hydrocarbons such as benzene, toluene, and xylene. The fat-soluble solvent may be preferably halogenated hydrocarbons, and more preferably dichloromethane.

The amount of the fat-soluble solvent is not particularly limited as long as it is an amount capable of dissolving polymer, and may vary depending on the types of polymer and fat-soluble solvent. For instance, it may be 0.1 to 10 times, preferably 0.5 to 4 times, and more preferably 1 to 2 times the weight of the polymer.

The oil phase (O) may be prepared by mixing a polymer in a fat-soluble solvent, and may be mixed using a stirrer, a mixer or a voltex if desired.

The W1/O emulsion is prepared by mixing an internal aqueous phase and an oil phase, while the mixing may be performed by known methods in the art. The mixing method may be, for example, a stirring method using a discontinuous shaking method, a propeller type stirrer, a turbine type stirrer, and the like; a colloid mill method; a homogenizer method; or an ultrasonic method, while a homogenizer method is preferred. The W1/O emulsion as used herein can be prepared by a method in which an inner aqueous phase is preferably added to an oil phase and homogenized with a homogenizer.

The mixing ratio of the inner aqueous phase and the oil phase may vary depending on the kinds of polymer, leuprolide, aqueous solvent and fat-soluble solvent. For example, it is not limited to, but may be 1 to 100 parts by weight of the oil phase, preferably 1 to 20 parts by weight of the oil phase, more preferably 5 to 15 parts by weight of the oil phase, per 1 part by weight of the inner aqueous phase.

After the step (i), the resulting W1/O emulsion may be optionally cooled. The cooling temperature may be 10° C. to 20° C., preferably 15° C. to 18° C.

In step (ii), the W1/O emulsion prepared in step (i) is dispersed in a polyvinyl alcohol aqueous solution (W2) to prepare a W1/O/W2 emulsion.

The temperature of the polyvinyl alcohol aqueous solution is preferably 18° C. or less, more preferably in the range of 10° C. to 18° C.

The aqueous polyvinyl alcohol solution of step (ii) may further contain an osmotic pressure regulator. The osmotic pressure regulator contained in the polyvinyl alcohol aqueous solution in the step (ii) is not limited as long as it produces an osmotic pressure in an aqueous solution. For example, it may include water-soluble polyhydric alcohol; water-soluble monohydric alcohol; water-soluble monosaccharides, disaccharides and oligosaccharides or derivatives thereof; water-soluble amino acids; water-soluble peptides, proteins or derivatives thereof; and the like. Among these, water-soluble polyhydric alcohols and water-soluble monosaccharides, disaccharides and oligosaccharides or derivatives thereof are preferable. Water-soluble polyhydric alcohols and water-soluble monosaccharides are more preferred, while water-soluble polyhydric alcohols are most preferred. Examples of the water-soluble polyhydric alcohol include dihydric alcohols (such as glycerin), pentahydric alcohols (such as arabitol, xylitol, and adonitol), hexahydric alcohols (such as mannitol, sorbitol, and dulcitol), and the like. Among these alcohols, hexahydric alcohols are preferred, while mannitol is particularly preferred. Examples of water-soluble monohydric alcohols include methanol, ethanol, isopropyl alcohol and the like, while ethanol is preferred. Examples of the water-soluble monosaccharides include pentoses (e.g., arabinose, xylose, ribose, and 2-deoxyribose) and hexoses (e.g., glucose, fructose, galactose, mannose, sorbose, rhamnose, and fucose), while hexoses are preferred. Examples of the water-soluble disaccharides include maltose, cellobiose, a, a-trehalose, lactose, sucrose and the like, while lactose and sucrose are preferred. Examples of the water-soluble oligosaccharides include trisaccharides (e.g., maltotriose and raffinose) and tetrasaccharides (e.g. stachyose), while trisaccharides are preferred. Examples of the derivatives of monosaccharides, disaccharides and oligosaccharides mentioned above include glucosamine, galactosamine, glucuronic acid, galacturonic acid and the like. Examples of the above-mentioned water-soluble amino acids include neutral amino acids (such as glycine, alanine, valine, leucine, isoleucine, phenylalanine, tyrosine, tryptophan, serine, threonine, proline, hydroxyproline, cysteine, and methionine), acidic amino acids (such as aspartic acid and glutamic acid), and basic amino acids (such as lysine, arginine, and histidine). These water-soluble amino acids can also be used as salts with acids (e.g., hydrochloric acid, sulfuric acid, and phosphoric acid) or with alkali (for instance, alkali metals such as sodium and potassium). Examples of the water-soluble peptides, proteins or derivatives thereof include casein globulin, prolamin, albumin, gelatin and the like.

Preferably, the osmotic pressure regulator according to the present invention may be D-mannitol, sorbitol, trehalose, glucose and the like, most preferably D-mannitol.

In the step (ii), the osmotic pressure regulator contained in the polyvinyl alcohol aqueous solution may be contained in an amount of 0.01 to 7% by weight, preferably 0.1 to 6% by weight, and most preferably 0.5 to 5% by weight.

In step (iii), the obtained W1/O/W2 emulsion is dried to prepare and recover microspheres.

The drying can be carried out by conventional methods generally used for removing solvent from prepared microspheres. For example, the prepared microspheres may be simply stirred, heated, treated with nitrogen gas or the like, stirred under reduced pressure, or evaporated under controlled vacuum conditions to evaporate solvent. Preferably, the prepared microspheres may be dried by an in-water drying method in which solvent is removed by stirring under reduced pressure.

As used herein, the recovery means to separate and obtain microspheres from the aqueous phase, and may be carried out by conventional methods such as centrifugation and filtration, in which solid components are separated from the aqueous phase.

The microspheres prepared in the step (iii) may be further subjected to a washing step in which the microspheres are re-dispersed in distilled water or the like, mixed, and recovered. Through the above-described washing step, drug residues on the surface of the microspheres can be removed.

Furthermore, the microspheres prepared according to the present invention may be solidified by a method such as freeze-drying to obtain more stable microspheres. More preferably, the prepared microspheres may be suspended in a suitable solution such as water for injection, solidified by mixing with known excipients (for example, sugars such as mannitol), a dispersing agent and the like, followed by freeze-drying.

As used herein, the size of "the leuprolide-containing microsphere" may be 300 μm or less in diameter, preferably 1 μm to 200 μm in diameter, and most preferably 1 μm to 100 μm.

As used herein, the amount of leuprolide as contained in the leuprolide-containing microsphere may be 5 wt % to 20 wt %, preferably 7 wt % to 15 wt %, on the basis of a total weight of the microsphere.

In the pharmaceutical composition of the present invention, the amount of leuprolide provided in the form of a leuprolide-containing microsphere of a sustained-release pharmaceutical preparation is preferably 75% to 99.999% by weight, more preferably 80 wt % to 99.9 wt %, on the basis of a total amount of active ingredients contained in the pharmaceutical composition.

Specifically, the pharmaceutical composition according to the present invention is characterized by its significantly rapid action with its Tmax of 50 to 70 minutes, considering that preparations comprising leuprolide-containing microspheres prepared by the known methods reach their maximum blood concentration 3 to 4 hours after their administration (See YASUAKI OGAWA et al., 1989).

In addition, the pharmaceutical composition of the present invention is characterized by its long duration of action for 3 weeks or longer, eliminating the inconvenience of daily administration which is a problem of conventional rapid-acting injections. Preferably, the duration of action of the pharmaceutical composition according to the present invention may be from 3 weeks to 6 months.

As used herein, the term "Tmax" refers to the time to peak plasma concentration, meaning the time it takes the drug (i.e. leuprolide) to reach its maximum plasma concentration after administration of the pharmaceutical composition according to the present invention.

As used herein, the term "Cmax" refers to the maximum plasma concentration, meaning the maximum plasma concentration of the drug (i.e. leuprolide) due to the administration of the pharmaceutical composition according to the present invention.

As used herein, the term "AUC" refers to the area under the plasma concentration-time curve. In pharmacokinetics, the term "AUC" means the area under the curve obtained by plotting the serum concentration of a beneficial agent (a drug or an active ingredient) against the time taken from the start of administration to the time "t". In normal drug administration, AUC is the area under the curve over the period of administration with doses administered periodically to infinity. AUC can be obtained by analyzing serum samples of a subject to be administered.

The pharmaceutical composition of the present invention is characterized by comprising leuprolide per se and leuprolide-containing microspheres at a specific ratio, leading to the rapid action of its pharmaceutical effect, with which the drug can be rapidly exposed in a sufficient amount shortly after its administration to exert its pharmaceutical effect, in combination with its sustained action for 4 weeks or longer. That is, the present invention relates to a composition characterized by having the effects of both rapid-acting and sustained-release injectable preparations, wherein, upon its administration, the composition achieves an initial exposure of a sufficient amount of the drug (i.e., leuprolide) via its very high initial release rate, that is, an increase in Cmax, a shortening of Tmax (time to peak plasma concentration), and an increase in initial AUC, while the blood concentration of the drug sustains for four weeks or longer in a single injection.

The composition according to the present invention resolves the inconvenience of the conventional rapid-acting injections containing leuprolide which are required to be administered daily to maintain the drug efficacy due to its short half-life upon being subcutaneously or intramuscularly injected. While the conventional sustained-release preparations are aimed at resolving the problem of such rapid-acting injections and are thus able to maintain the sustained level of the drug in the blood, The composition according to the present invention also solves the problem of such conventional sustained-release preparations which are unable to achieve a sufficient level of drug exposure at the initial stage of administration to target sites. Hence, the composition according to the present invention exhibits an unpredictably high drug efficacy compared to those of the prior art, which is well illustrated in the following examples.

The pharmaceutical composition according to the present invention is one used for the prophylaxis and treatment of a sex hormone-dependent benign or malignant disease. As used herein, the sex hormone-dependent benign or malignant disease is not particularly limited as long as it is a disease known in the art, for instance, benign prostate enlargement, prostate cancer, precocious puberty, excessive hair growth, endometrial hyperplasia and its accompanying symptoms, endometrial cancer, external fertilization (IVF/COS/ART), contraception, premenstrual syndrome (PMS), uterine myoma, breast cancer, proximal tubal obstruction (PTO), ovarian cancer, uterine cancer, and the like.

The method of administering the pharmaceutical composition of the present invention is not limited as long as it is suitable for a patient in view of the severity of the disease, age, sex and other conditions of the patient. The routes of administration preferably include, but are not limited to, subcutaneous, intradermal, intravenous, intramuscular, intraperitoneal injections and the like.

Advantageous Effect

The pharmaceutical composition of the present invention is characterized in that it simultaneously possesses both the rapid-acting property of the contained drug which enables the quick exposure of the sufficient amount of the drug at the initial stage of administration (about 1 hour after administration), and the sustained release property of 3 weeks or longer, leading to its effectiveness in the prevention and treatment of sex hormone-dependent benign or malignant diseases.

BRIEF DESCRIPTION OF THE DRAWINGS

FIG. 1 shows the plasma concentration of leuprolide acetate (expressed as Plasma concentration) over time after administration of injectable preparations in each different composition to SD Rats at a total active ingredient dose of 3 mg/kg.

FIG. 2 shows the plasma concentration of leuprolide acetate (expressed as Plasma concentration) over time after administration of the injectable preparation of Example 4 to SD Rat.

DETAILED DESCRIPTION OF THE INVENTION

Hereinafter, the present invention will be described in detail. However, the following examples are illustrative of the present invention only, and the contents of the present invention are not limited to the following examples.

<Preparation Examples 1, 3 and 4> Preparation of Leuprolide-Containing Microspheres 0.5 mL of distilled water was added to 0.50 g of leuprolide acetate powder (Polypeptide Laboratories) and 0.08 g of gelatin mixture. A W1 solution was then prepared by dissolving the powder while heating to about 60° C. 6.0 mL of dichloromethane was added to 4.0 g of DL-lactic acid-glycolic acid copolymer (7525, Inherent Viscosity 0.17 dl/g) powder, followed by voltexing to prepare an 0 solution. The W1 solution was added to the 0 solution, followed by emulsification with a homogenizer to prepare a W1/O emulsion.

The W1/O phase was cooled using a chiller maintained at 15-18° C. and mixed with 0.25 wt % of a polyvinyl alcohol (PVA) aqueous solution adjusted to 15-18° C. Then, the mixture was stirred at 6500 rpm (Preparation Example 1), 6000 rpm (Preparation Example 3), and 5500 rpm (Preparation Example 4) to prepare W1/O/W2 emulsions, respectively. The resulting W1/O/W2 emulsions were dried in water for 4 hours, filtered through mesh with 75 μm apertures, and centrifuged to recover microspheres. The recovered microparticles were re-dispersed with distilled water. Subsequently, after mixing, they were repeatedly centrifuged to wash the surface of the microparticles sufficiently and recovered. The recovered microparticles were then freeze-dried to obtain polymer microspheres. The content of leuprolide in the obtained microspheres was 9.45% (Preparation Example 1), 9.33% (Preparation Example 3) and 9.55% (Preparation Example 4), respectively, by weight.

<Preparation Examples 2 and 5> Preparation of Leuprolide-Containing Microspheres 0.5 mL of distilled water was added to 0.50 g of leuprolide acetate powder and 0.08 g of gelatin mixture. A W1 solution was prepared by dissolving the powder while heating to about 60° C. 6.0 mL of dichloromethane was added to 4.0 g of DL-lactic acid-glycolic acid copolymer (7525, Inherent Viscosity 0.17 dl/g) powder, followed by voltexing to prepare an 0 solution. The W1 solution was added to the 0 solution, followed by emulsification with a homogenizer to prepare a W1/O emulsion.

The W1/O phase was cooled using a chiller maintained at 15-18° C. and mixed with 0.25 wt % of a polyvinyl alcohol (PVA) aqueous solution (1 wt % of D-mannitol is contained in Preparation Example 2, while 8 wt % of D-mannitol in Preparation Example 5) adjusted to 15-18° C. Then, the mixture was stirred at 5000 rpm to prepare a W1/O/W2 emulsion. The resulting W1/O/W2 emulsion was dried in water for 4 hours, filtered through mesh with 75 μm apertures, and centrifuged to recover microspheres. The recovered microparticles were re-dispersed with distilled water. Subsequently, after mixing, they were repeatedly centrifuged to wash the surface of the microparticles sufficiently and recovered. The recovered microparticles were then freeze-dried to obtain polymer microspheres. The content of leuprolide in the obtained microspheres was 9.93% (Preparation Example 2) and 7.79% (Preparation Example 5), respectively, by weight.

<Examples 1, 2, 3, and 4> Preparation and Efficacy Evaluation of Injectable Formulations Comprising Leuprolide-Containing Microspheres and Leuprolide Acetate While designating the microspheres obtained by <Preparation Example 1> as Comparative Example 1, injectable preparations of Examples 1 and 2, which were prepared by mixing the microspheres of <Preparation Example 1> and leuprolide acetate as active ingredients in an amount described in Table 1, were administered via subcutaneous injection to SD Rats, respectively.

In addition, While designating the microspheres obtained by <Preparation Example 2> as Comparative Example 2, injectable preparations of Examples 3 & 4 and Comparative Example 3, which were prepared by mixing the microspheres of <Preparation Example 2> and leuprolide acetate as active ingredients in an amount described in Table 2, were administered via subcutaneous injection (Comparative Examples 2 & 3, and Example 4) or intramuscular injection (Example 3) to SD Rats, respectively.

TABLE 1

|  | Comparative Example 1 | Example 1 | Example 2 |
|---|---|---|---|
| Amount of leuprolide administered in microspheres | 3 mg/kg | 2.73 mg/kg | 2.5 mg/kg |
| Amount of leuprolide acetate administered | 0 mg/kg | 0.27 mg/kg | 0.5 mg/kg |
| Cmax (ng/ml) | 29.87 ± 8.31 | 148.80 ± 36.44 | 261.51 ± 16.48 |
| $AUC_{8-72\ hr}$ (ng hr/ml) | 75.3 | 140.0 | 99.7 |
| Tmax (hr) | 3 hr | 1 hr | 1 hr |

TABLE 2

|  | Comparative Example 2 | Example 3 | Example 4 | Comparative Example 3 |
|---|---|---|---|---|
| Amount of leuprolide administered in microspheres | 3 mg/kg | 2.73 mg/kg | 2.61 mg/kg | 2.31 mg/kg |
| Amount of leuprolide acetate administered | 0 mg/kg | 0.27 mg/kg | 0.39 mg/kg | 0.69 mg/kg |
| Cmax (ng/ml) | 22.75 ± 4.48 | 151.25 ± 14.86 | 266.50 ± 95.30 | 361.35 ± 52.02 |
| $AUC_{8-72\ hr}$ (ng hr/ml) | 155.0 | 327.12 | 161.4 | 24.7 |
| Tmax (hr) | 3 hr | 1 hr | 1 hr | 1 hr |

As shown in FIG. 1, in comparison with Comparative Example 1, it was confirmed from Comparative Example 3 that as the dose of leuprolide acetate out of the total dose increased, Cmax was able to be increased. However, it was found that, in Comparative Example 3, the plasma concentration of leuprolide acetate rapidly decreased following initial Cmax due to its short half-life.

Therefore, it was verified that, in order to simultaneously obtain the increased Cmax and initial AUC, it is necessary to increase the initial release rate of leuprolide acetate-containing microspheres, while the compositional ratio of rapid-acting leuprolide acetate and leuprolide-encapsulated microspheres is very important, as shown in FIG. 1 and Example 4.

In addition, as shown in the above Table 2, the present inventors confirmed that the composition according to the present invention possessing both the increased Cmax & $AUC_{8-72\ h}$ and the shortened Tmax (Time to Peak Plasma Concentration) may be prepared as shown in Examples 3 & 4.

<Examples 5 and 6> Preparation and Efficacy Evaluation of Injectable Formulations Comprising Leuprolide-Containing Microspheres and Leuprolide Acetate Injectable preparations were prepared by mixing the microspheres of <Preparation Example 3> and leuprolide acetate, the microspheres of <Preparation Example 4> and leuprolide acetate, and the microspheres of <Preparation Example 5> and leuprolide acetate as active ingredients in an amount described in Table 3, resulting in preparing those of Example 5, Example 6 and Comparative Example 4, respectively. Subsequently, the obtained injectable preparations were intramuscularly injected to SD male Rats, respectively.

TABLE 3

|  | Example 5 | Example 6 | Comparative Example 4 |
|---|---|---|---|
| Amount of leuprolide administered in microspheres | 2.86 mg/kg (Preparation Example 3) | 2.86 mg/kg (Preparation Example 4) | 2.5 mg/kg (Preparation Example 5) |
| Amount of leuprolide acetate administered | 0.14 mg/kg | 0.14 mg/kg | 0.5 mg/kg |

TABLE 3-continued

|  | Example 5 | Example 6 | Comparative Example 4 |
|---|---|---|---|
| Cmax (ng/ml) | 146.50 ± 17.33 | 121.90 ± 23.52 | 169.00 ± 16.59 |
| $AUC_{8-72\ hr}$ (ng hr/ml) | 300.70 | 380.86 | 82.45 |
| Tmax (hr) | 1 hr | 1 hr | 1 hr |

INDUSTRIAL APPLICABILITY

As described above, the present invention relates to a pharmaceutical composition comprising leuprolide acetate with both immediate and sustained release properties. More particularly, the present invention relates to a pharmaceutical composition comprising 0.001 wt % to 25 wt % of leuprolide as an immediate release preparation, and 75 wt % to 99.999 wt % of leuprolide as contained in a microsphere as a sustained release preparation, on the basis of a total weight of active ingredients.

The above described pharmaceutical composition according to the present invention is characterized in that it simultaneously possesses both the rapid-acting property of the contained drug which enables the quick exposure of the sufficient amount of the drug at the initial stage of administration, and the sustained release property of 4 weeks or longer. Thus, the pharmaceutical composition according to the present invention is effective in the prevention and treatment of sex hormone-dependent benign or malignant diseases, leading to its highly industrial applicability.

The invention claimed is:

1. A method for preparing a pharmaceutical composition, the method comprising the steps of:
   (a) preparing an immediate release part comprising leuprolide as a first active ingredient;
   (b) preparing a sustained release part comprising leuprolide contained in a microsphere as a second active ingredient, wherein the microsphere is prepared by the steps of:
      (i) mixing an inner aqueous phase (W1) containing leuprolide, a thickener and an aqueous solvent with an oil phase (O) containing a polymer and a fat-soluble solvent to obtain a W1/O emulsion;
      (ii) dispersing the W1/O emulsion of step (i) in a polyvinyl alcohol aqueous solution (W2) to obtain a W1/O/W2 emulsion; and
      (iii) drying and recovering the W1/O/W2 emulsion prepared in step (ii); and
   (c) mixing the immediate release part and the sustained release part in a pharmaceutically acceptable carrier to form a pharmaceutical composition, wherein the immediate release part comprises 0.1% to 20% of a total amount of leuprolide in the pharmaceutical composition and wherein the microsphere of the sustained release part comprises 80% to 99.9% of the total amount of leuprolide in the pharmaceutical composition; and wherein the ratio of leuprolide in the immediate release part to leuprolide in the microsphere of the sustained release part is determined to achieve both immediate and sustained release properties.

2. The method of claim 1, wherein Time to Peak Plasma Concentration (Tmax) of the composition is 50 to 70 minutes.

3. The method of claim 1, wherein the duration of action of the active ingredients in the composition is four weeks or longer.

4. The method of claim 1, wherein the thickener is selected from the group consisting of gelatin, albumin, pectin, agar, cellulose, dextrin, xanthan gum and mixtures thereof.

5. The method of claim 1, wherein the polyvinyl alcohol aqueous solution of step (ii) contains 0.01 to 7% by weight of an osmotic pressure regulator, on the basis of a total weight of the composition.

6. The method of claim 5, wherein the osmotic pressure regulator is selected from the group consisting of pentahydric alcohol, hexahydric alcohol, water-soluble monohydric alcohol, water-soluble monosaccharide, water-soluble disaccharide, water-soluble oligosaccharide or derivatives thereof, and water-soluble amino acid.

* * * * *